United States Patent [19]
Sreenivasan et al.

[11] Patent Number: 5,981,775
[45] Date of Patent: Nov. 9, 1999

[54] PROCESS FOR THE PREPARATION OF ISOFLAVONES

[75] Inventors: Balasubramanian Sreenivasan, Nanganullur, India; Muraleedharan G. Nair, Okemos, Mich.

[73] Assignee: Board of Trustees operating Michigan State University, East Lansing, Mich.

[21] Appl. No.: 09/154,230

[22] Filed: Sep. 16, 1998

[51] Int. Cl.$^6$ .................................................. C07D 311/04
[52] U.S. Cl. ............................................................ 549/403
[58] Field of Search ............................................. 549/403

[56] References Cited

U.S. PATENT DOCUMENTS

| | | |
|---|---|---|
| 5,085,682 | 2/1992 | Safir et al. . |
| 5,125,955 | 6/1992 | Safir et al. . |
| 5,149,866 | 9/1992 | Chiou et al. . |
| 5,691,275 | 11/1997 | Nair et al. . |

OTHER PUBLICATIONS

Sekizaki, H., et al., Studies on Zoospore Attracting Activity. II. Synthesis of Isoflavones and Their Activity to Aphanomyces euteiches Zoospore. Biol Pharm Bull. 16:698 (1993).

Miles, C.O., et al., Aust. J. Chem 42:1103 (1989).

Alcantara, A.R., et al., Tetrahedron Letters 28:1515 (1987).

Pelter, Andrew, et al., Synthesis, 5:326 (1976).

Chang, Y–C., et al., J. Agric. Food Chem. 42:1869 (1994).

Wahala, K. et al., J. Chem. Soc Perkin Trans I, 3005 (1991).

Kagal, S.A., et al., Tetrahedron Letters, 14:593 (1962).

Jha, H., et al., Angew. Chem Int. Ed. Engl. 20:102 (1981).

Chemical Abstracts 118:38593 (1993).

*Primary Examiner*—Amelia Owens
*Attorney, Agent, or Firm*—Ian C. McLeod

[57] ABSTRACT

A process for the preparation of an isoflavone from a 2'-hydroxydeoxybenzoin(I) is described. The process uses prepared N,N'-dimethyl(chloromethylene) ammonium chloride as a reactant with (I) in borontrifluoride etherate or other Lewis acid as a solvent. The isoflavones are known biologically active compounds.

23 Claims, 2 Drawing Sheets

Friedel Crafts Acylation Catalyst:
$BF_3 \cdot Et_2O$ or $POCl_3-ZnCl_2$

N,N'-dimethyl(chloromethylene)ammonium chloride is generated by the action of $PCl_5$ on DMF. This species could be generated in a similar way by reacting $POCl_3$ or Methane sulfonyl chloride or P-toluene sulfonyl chloride with DMF.

PROCESS FOR THE PREPARATION OF ISOFLAVONES

BACKGROUND OF THE INVENTION (1). Field of the Invention

This invention relates to a process for the preparation of isoflavones and in particular formononetin. The process involves reaction of a 2-hydroxy-deoxybenzoin with N,N'-dimethyl (chloromethylene)ammonium chloride to form the isoflavone. This invention particularly relates to either a "one pot" or a two step process involving the initial formation of 2,4-dihydroxy-4'-methoxydeoxybenzoin followed by its conversion to formononetin.

(2). Description of Related Art

Isoflavones are important compounds which are used for a variety of biological purposes. In particular, formononetin (MYCOFORM, VamTech, L.L.C., okemos, Mich.) is a potent vesicular-arbuscular mycorrhizal stimulating compound (U.S. Pat. Nos. 5,085,682, 5,125,955 to Safir et al; Taiwan Patent No. 60604 to Safir et al; U S. Pat. No. 5,691,275 to Nair, et al; Nair, M. G., et al, Applied and Environmental Microbiology 57:434 (1991); Siqueira, J. O., et al., Plant and Soil, 134:233 (1991); and Siqueira, J. O., et al., The New Phytologist, 118:87 (1991)). Formononetin is under extensive field trials on corn, soybean and horticultural crops around the world. The prior art procedures for the production of isoflavones are not economical.

The synthesis of formononetin, which is the preferred isoflavone and is representative, from the corresponding chalcone is a known process. The method (Sekizaki, H., et al., Studies on Zoospore Attracting Activity. II. Synthesis of Isoflavones and Their Activity to *Aphanomyces euteiches Zoospore*. Biol. Pharm. Bull. 16:698 (1993)) involves the oxidative rearrangement of 2'-hydroxy-4-methoxy-4-(tetrahydropyran-2-yloxy)chalcone by thallium (III) nitrate trihydrate (TTN) in methanol. In spite of the simplicity of this reaction, the overall method suffers from the fact that three steps are required to prepare the starting material 2'-hydroxy-4-methoxy-4-(tetrahydropyran-2-yloxy) chalcone. The method also has the drawback of selective protection (Miles, C. O., et al., Aust. J. Chem 42:1103 (1989)) and deprotection of one of the hydroxyl groups in ring A (benzene ring) of the chalcone. Even with the best method available (Alcantara, A. R., et al., Tetrahedron Letters 28:1515 (1987)) for the condensation of 2-hydroxy-4-(tetrahydropyran-2-yloxyl)acetophenone and p-anisaldehyde the yield was only 64%. Further, this methodology has serious drawbacks such as (a) the use of an expensive and very toxic reagent, thallium (III) nitrate trihydrate (TTN) in excess and (b) the low yield (52%) of formononetin which could be obtained in pure form only after column chromatographic purification.

Another known approach used for the synthesis of formononetin is the general method involving the addition of one carbon to 2-hydroxydeoxybenzoins and their cyclization to form isoflavones. The method introduced by Andrew Pelter (Pelter, Andrew, et al., Synthesis, 5:326 (1976)) involves the reaction of 2-hydroxydeoxybenzoins with N,N-dimethylformamide dimethylacetal (dimethoxydimethyl aminomethane) (two equivalents) in dry benzene. Refluxing a mixture of 2,4-dihydroxy-4'-methoxydeoxybenzoin with N,N-dimethylformamide dimethyl acetal in dry benzene for 4 hours gave formononetin in 85% yield. However, the use of the expensive reagent, N,N-dimethylformamide dimethyl acetal and dry benzene as solvent makes this an unattractive method for the commercial production of formononetin.

A modified version of the above method-microwave mediated synthesis of anticarcinogenic isoflavones from soybeans (Chang, Y-C., et al., J. Agric. Food. Chem 42:1869 (1994)) gave 91% in the case of formononetin. However, this method is totally unsuitable for the large scale preparation due to the fact that microwave mediated reactions are efficient so far in very small scale and possibly in gram quantities. This method has the additional disadvantage of using large excess of N,N-dimethylformamide dimethyl acetal and an equal amount of THF and the requirement of a special reaction vessel to carry out the reaction under microwave conditions.

Another reported method (Wahala, K, et al., J. Chem. Soc Perkin Trans I, 3005 (1991)) involving the in situ formation of deoxybenzoin and its conversion to isoflavones required a large excess of borontrifluoride etherate, dry DMF, and methanesulfonyl chloride under argon atmosphere. All of the reactions are in situ. The experimental conditions, workup procedures, the use of large excess of borontrifluoride etherate and purification by column chromatography to obtain the final product make this method unsuitable for large scale preparations.

A different approach utilizing the modified Vilsmeyer-Haack reaction (Kagal, S. A., et al., Tetrahedron Letters, 14:593 (1962)) has the greatest disadvantage due to the formation of polymeric products along with the unreacted starting material and the reaction required heating (~120° C.) for 19 hours. The time consumption and laborious purification procedures make this method a poor choice for large scale preparation even though relatively inexpensive reagents like DMF and phosphorous oxychloride are used in the process.

The method involving the use of 1,3,5-triazine (Jha, H., et al., Angew. Chem Int. Ed. Engl, 20:102 (1981)) in glacial acetic acid, borontrifluoride etherate and acetic anhydride gave formononetin in 91% yield. However, the purification by column chromatography and the use of expensive reagents like 1,3,5-triazine (2 equivalents) makes this method unsuitable for commercial scale production of formononetin.

2,4-Dihydroxy-4'-methoxydeoxybenzoin was prepared by the Fridel Crafts acylation of resorcinol with p-methoxyphenylacetic acid and borontrifluoride etherate in excess. In this reaction, $BF_3$ etherate was used as a Lewis acid and the solvent for the reaction (Wahala, K., et al., J. Chem. Soc. Perkin Trans I, 3005 (1991)). Another known procedure involved the Hoesch reaction (Organic Synthesis, Collective Volumes, Volume II, P-522, Organic Reactions 5:387 (1949)) of resorcinol with p-methoxyphenyl acetonitrile. However, this procedure is laborious, time consuming and gives poor yield of deoxybenzoin.

A number of methods are available for the preparation of p-methoxyphenylacetic acid and almost all published processes deal with the initial preparation of p-methoxyphenylacetonitrile (Synthesis of p-Methoxyphenylacetonitrile, organic Synthesis, Collective Volumes, Volume IV John Wiley & Sons, Inc. P-576, (1963)) followed by it's hydrolysis. p-Methoxyphenylacetonitrile has been prepared from either methoxybenzyl alcohol or methoxybenzene or p-methoxybenzaldehyde to form p-methoxy benzyl chloride which is then treated with sodium cyanide. Since more than three steps are involved and each step yielding the product in 50–95%, the overall yield of p-methoxyphenyl acetic acid is always less than 60%. These procedures also have the disadvantage of using toxic materials like sodium cyanide, long reaction times and cumbersome isolation procedures. Another known procedure is by the modified Willgerodt reaction (U.S. Pat. No. 5,149,866, Chemical Abstracts 118:38593 (1993); Schwenk, E., et al., J. Org. Chem 11:798 (1946)) which involves the initial preparation of thioaceto-morpholide from p-methoxyacetophenone and it's hydrolysis to form p-methoxyphenyl acetic acid. The thioacetomorpholide is prepared by refluxing a mixture of p-methoxy acetophenone, sulfur and morpholine and the hydrolysis is done by refluxing the thioacetomorpholide with alcoholic sodium hydroxide (10 hours) followed by acidification. The product is extracted with diethyl ether and recrystallized from dilute alcohol or water. A reduction in reaction time and the modification of experimental procedures would make this process a better method for the preparation of p-methoxyphenylacetic acid.

OBJECTS

It is therefore an object of the present invention to provide a process for the preparation of isoflavones. It is particularly an object of the present invention to provide a process for the preparation of formononetin using the starting material p-methoxyacetophenone. It is a particular object of the present invention to prepare isoflavones in high purity, in high yield and using inexpensive reagents within a very short period of time and especially without the use of laborious purification methods. These and other objects will be come increasingly apparent by reference to the following description and the drawings.

SUMMARY OF THE INVENTION

The present invention relates to a process for the preparation of an isoflavone which comprises: adding a preformed N,N'-dimethyl(chloromethylene) ammonium chloride to a 2-hydroxydeoxybenzoin in a Lewis acid as a solvent to produce the isoflavone; and separating the isoflavone from the reaction mixture.

The present invention also relates to a process for producing an isoflavone which comprises: reacting in a reaction mixture a ketone of the formula:

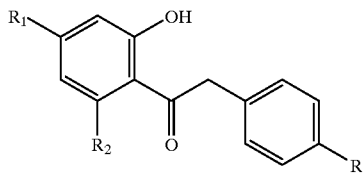

with preformed N,N'-dimethyl(chloromethylene) ammonium chloride in borontrifluoride etherate as a solvent where R is selected from the group consisting of hydrogen, hydroxyl and methoxy, $R_1$ is selected from the group consisting of hydrogen and hydroxyl and $R_2$ is selected from the group consisting of methoxy, hydrogen and hydroxyl to produce an isoflavone of the formula:

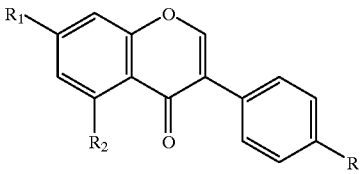

wherein R, $R_1$ and $R_2$ are as set forth previously; and separating the isoflavone from the reaction mixture.

The following isoflavones in Table 1 are particularly prepared by the process of the present invention.

TABLE 1

|  | R | $R_1$ | $R_2$ |
|---|---|---|---|
| Formononetin | OMe | OH | H |
| Biochanin A | OMe | OH | OH |
| Daidzein | OH | OH | H |
| Genistein | OH | OH | OH |

The process for the preparation of formononetin comprises the preparation of p-methoxyphenylacetic acid and its reaction with resorcinol to form 2,4-dihydroxy-4'methoxydeoxybenzoin followed by the formation of formononetin. The present invention is an improvement over the known processes for the preparation of formononetin. The improvement consists of a "one pot" reaction to yield formononetin. Also, it comprises a two-step process involving the reaction of resorcinol with p-methoxyphenylacetic acid in the presence of a Lewis acid to form 2,4-dihydroxy-4'-methoxydeoxybenzoin and its treatment with N,N'-dimethyl(chloromethylene) ammonium chloride (formed by activating DMF) to form formononetin in high yield and purity (FIGS. 1 and 2). The improvement also comprises further modification of the Willgerodt reaction to produce p-methoxyphenylacetic acid in high purity and in less reaction time.

DESCRIPTION OF PREFERRED EMBODIMENTS

The preferred process involves the production of formononetin. The reaction involving the preparation of 2,4-dihydroxy-4'-methoxydeoxybenzoin followed by its conversion to formononetin is described. Also, the preparation of p-methoxy phenylacetic acid, the raw material for the production of 2,4-dihydroxy-4'-methoxydeoxybenzoin, has been modified. This step is now a part of the overall modified process for the manufacture of formononetin.

Figure 1:
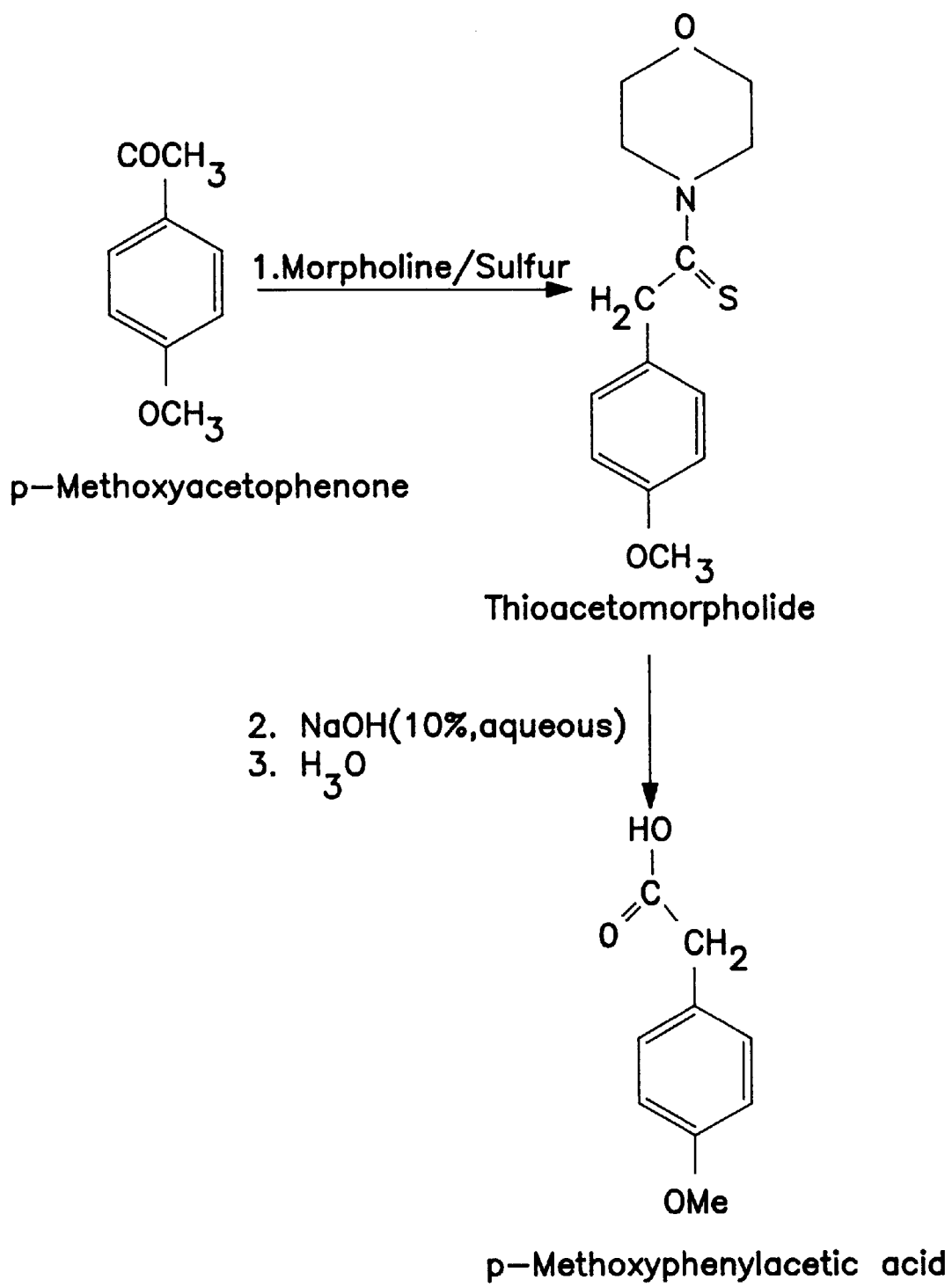
FIG. 1 is a schematic of a reaction for forming p-methoxyphenylacetic acid from p-methoxyacetophenone.
Figure 2:
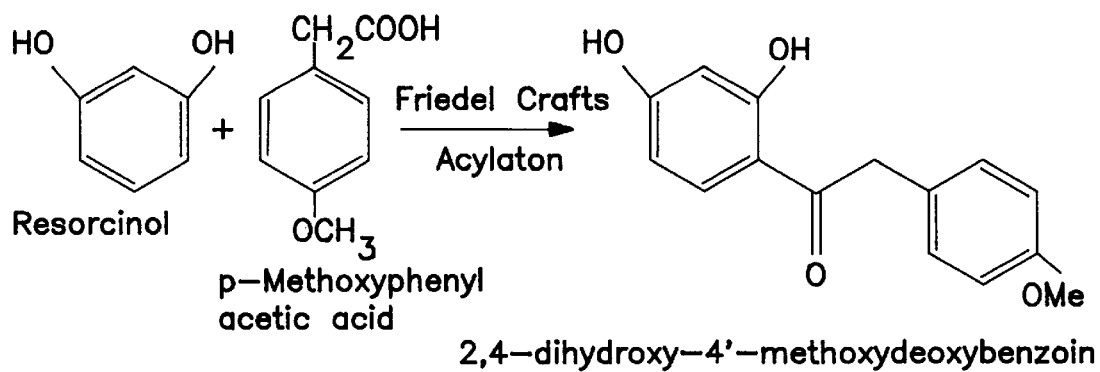
FIG. 2 is a schematic of the reaction steps of the method of the present invention for the preparation of formononetin where the p-methoxyphenyl acetic acid is used as a starting compound.
Figure 2:
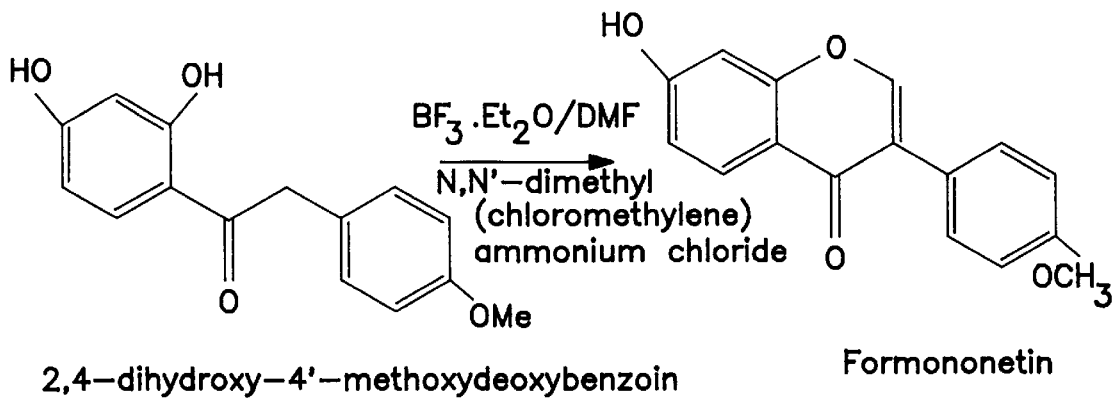
Figure 2:
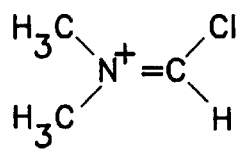

In a preferred embodiment of the process of the invention, the synthesis of formononetin is carried out as follows.

a) Preparation of p-methoxyphenylacetic Acid:

The first step in the overall process is the preparation of p-methoxyphenylacetic acid from p-methoxyacetophenone by the modified method of Willgerodt reaction as shown in FIG. 1. In particular, the modification is with respect to the hydrolysis of thioacetomorpholide to p-methoxyphenyl acetic acid. According to the modified method, the hydrolysis is carried out in 4 hours or less by treating the thioacetomorpholide in 10% aqueous NaOH solution. The completion of the reaction is noted by the disappearance of thioacetomorpholide (which remains as an oil under refluxing conditions) and by the formation of a clear solution. The alkaline solution is then filtered to remove any trace amount of sulfur present in the thioacetomorpholide. This alkaline solution is then acidified with concentrated HCl. The precipitated p-methoxyphenylacetic acid is filtered off and washed well with cold water. The washings are combined with the mother liquor and concentrated to less than one third of the original volume. The concentrated solution on standing yields a second crop of p-methoxyphenyl acetic acid. The product is recrystallized from hot water with the treatment of activated charcoal. The resulting p-methoxyphenyl acetic acid is a white plate-like crystalline product with a sharp melting point of 85–86° C. The overall yield of p-methoxyphenylacetic acid is 65–75%.

b) "One pot" preparation of Formononetin:

The preparation of formononetin is achieved either by a "one pot" process or by a two step process involving the isolation of 2,4-dihydroxy-4'-methoxydeoxybenzoin. In a "one pot" process, a mixture of p-methoxyphenylacetic acid and resorcinol is heated at 90° C. with borontrifluoride etherate (4–6 equivalents) for 1 hour. The reaction mixture is cooled to 10–15° C. and DMF is added dropwise. In another reaction vessel, N,N'-dimethyl(chloromethylene) ammonium chloride is prepared by treating DMF with phosphorous pentachloride. The DMF containing N,N'-dimethyl(chloromethylene) ammonium chloride is added to the above reaction mixture and the reaction is carried out at room temperature for 30 to 60 minutes. The dark orange-yellow solution is then poured slowly into boiling dilute HCl (0.1 N) with vigorous stirring and allowed to stand for 30 minutes. During this process, the yellow precipitate slowly becomes white with the formation of formononetin. The product is filtered off and washed well with water. Formononetin is finally purified by recrystallization from aqueous methanol, >99% purity with an overall yield of 85–95%.

The reagent, N,N'-dimethyl(chloromethylene) ammonium chloride, is prepared by treating DMF with (I) phosphorous oxychloride, (ii) methanesulfonyl chloride (iii) p-toluenesulfonyl chloride and (iv) polystyrenesulfonyl chloride.

In the two step process, the initial product, 2,4-dihydroxy-4'-methoxydeoxybenzoin is isolated, recrystallized and then used for the preparation of formononetin. A mixture of p-methoxyphenyl acetic acid and resorcinol is treated with either borontrifluoride etherate (4–6 equivalents) or phosphorous oxychloride-zinc chloride mixture (3–5 equivalents). The mixture is poured into NaOAc solution and the precipitated product is filtered off, washed with water and recrystallized from aqueous methanol with an overall yield of 90–95%.

2,4-dihydroxy-4'-methoxydeoxybenzoin is then treated with borontrifluoride etherate (3–5 equivalents), cooled to 10–15° C. and DMF added dropwise. As mentioned under the "one pot" method, N,N'-dimethyl(chloromethylene) ammonium chloride is prepared separately in DMF and added to the above reaction mixture. The workup procedure is similar to the "one pot" method. The overall yield of formononetin is 80–90%.

In order to fully illustrate the nature of the invention, and the manner of practicing the same, the following examples are presented.

EXAMPLE 1

Preparation of p-methoxyphenylacetic Acid

In a 500 mL RB flask fitted with a ref lux condenser, p-methoxyacetophenone (50 g, 0.33 mol), sulfur (16 g, 0.50 mol) and morpholine (43.4 g, 42.8 mL, 0.50 mol) were added. The mixture was then refluxed for 5 hours and the resulting dark brown viscous liquid was poured slowly into water, allowing the first addition to crystallize before the bulk was added. The crude thioacetomorpholide was ground thoroughly with water and filtered. The product was air dried to yield 77 g (92%) and the crude product was directly used for the hydrolysis.

In a one liter flask with a reflux condenser, crude thioacetomorpholide (50.0 g) was added to NaOH solution (10%, 400 mL) and the mixture was refluxed for 3 hours. The completion of the hydrolysis was confirmed by the disappearance of thioacetomorpholide (which remains as an oil under refluxing conditions) and with the formation of a clear solution. The solution was filtered to remove any trace amounts of sulfur present in thioacetomorpholide followed by acidification with concentrated HCl. The precipitated p-methoxyphenylacetic acid was filtered off and washed with cold water. The washing was combined with the mother liquor and concentrated to less than one third of the initial volume. The concentrated solution on standing at room temperature yielded a second crop of the product as needles. It was recrystallized from hot water with the treatment of activated charcoal and the resulting product was a white plate-like crystalline compound with a sharp melting point of 85–86° C. The overall yield of p-methoxyphenyl acetic acid was 72%.

EXAMPLE 2

"One pot" Preparation of Formononetin— Phosphorous Pentachloride Method.

In a 1 L three-necked RB flask fitted with a reflux condenser, a dropping funnel and stopper, p-methoxyphenylacetic acid (50.0 g, 0.3 mol), resorcinol (33.2 g, 0.3 mol) and borontrifluoride etherate (194 mL, 1.53 mol) were stirred with heating (90° C.) for 1 hour and cooled to 10° C. To this cooled solution ,DMF (230 mL) was added drop-wise with stirring. In another 500 mL RB flask fitted with a drying tube, DMF (390 mL) was cooled to 10° C. To this cooled DMF, phosphorous pentachloride ($PCl_5$, 93.9 g, 0.45 mol) was added in small portions and the mixture was allowed to stand at 55° C. for 10 minutes. This pale pink colored mixture containing N,N'-dimethyl (chloromethylene)ammonium chloride was then added to the above reaction mixture and the mixture was stirred at room temperature for 1 hour. The dark orange-yellow solution was then poured slowly into boiling dilute HCl (0.1 N) with vigorous stirring and allowed to stand for 30 minutes. During this process, the yellow precipitate slowly became white with the formation of formononetin. The product was filtered off and washed with water. The product was further purified by recrystallization from aqueous methanol giving a yield of 80% with a Melting point of 256–257° C. The $^1$H-NMR of this product was identical to an authentic sample of formononetin.

EXAMPLE 3

"One pot" Preparation of Formononetin—
Phosphorous Oxychloride Method.

In a 1 L three-necked RB flask fitted with a reflux condenser, a dropping funnel and stopper, p-methoxyphenylacetic acid (50.0 g, 0.3 mol), resorcinol (33.2 g, 0.3 mol) and borontrifluoride etherate (194 mL, 1.53 mol) were stirred with heating (90° C.) for 1 hour and cooled to 10° C. To this cooled solution, DMF (230 mL) was added dropwise with stirring. In another 500 mL RB flask fitted with a drying tube, DMF (390 mL) was cooled to 10° C. To this cooled DMF, phosphorous oxychloride ($POCl_3$, 83.8 mL, 138.35 g, 0.9 mol) was added drop-wise and the mixture was allowed to stand at room temperature for 20 minutes. This pale pink colored mixture containing N,N'-dimethyl (chloromethylene)ammonium chloride was then added to the above reaction mixture and the mixture was stirred at room temperature for 1 hour. The dark orange-yellow solution was then poured slowly into boiling dilute HCl (0.1 N) with vigorous stirring and allowed to stand for 30 minutes. During this process, the yellow precipitate slowly became white with the formation of formononetin. The product was filtered off and washed with water. The product was further purified by recrystallization from aqueous methanol giving a yield of 80%. The melting point was 256–257° C. The $^1$H-NMR of this product was identical to an authentic sample of formononetin.

EXAMPLE 4

"One pot" Preparation of Formononetin—
Methanesulfonyl Chloride Method.

In a 1 liter three necked RB flask fitted with a reflux condenser, a dropping funnel and stopper, p-methoxyphenylacetic acid (50.0 g, 0.3 mol), resorcinol (33.2 g, 0.3 mol) and borontrifluoride etherate (194 mL, 1.53 mol) were stirred with heating (90° C.) for 1 hour and cooled to 10° C. To this cooled solution, DMF (230 mL) was added dropwise with stirring. In another 500 mL RB flask fitted with a drying tube, DMF (390 mL) was cooled to 10° C. To this cooled DMF, methanesulfonyl chloride (72.2 mL, 106.8 g, 0.93 mol) was added dropwise and the mixture was allowed to stand at room temperature for 20 minutes. This mixture containing N,N'-dimethyl (chloromethylene) ammonium chloride was then added to the above reaction mixture and the mixture was stirred at room temperature for 1 hour. The dark orange-yellow solution was then poured slowly into boiling dilute HCl (0.1 N) with vigorous stirring and allowed to stand for 30 minutes. During this process, the yellow precipitate slowly became white with the formation of formononetin. The product was filtered off and washed with water. The product was further purified by recrystallization from aqueous methanol giving a yield of 80%. The melting point was 256–257° C. The $^1$H-NMR of this product was identical to an authentic sample of formononetin.

EXAMPLE 5

"One pot" Preparation of Formononetin—p-
toluenesulfonyl Chloride Method.

In a 1 L three-necked RB flask fitted with a reflux condenser, a dropping funnel and stopper, p-methoxyphenylacetic acid (50.0 g, 0.3 mol), resorcinol (33.2 g, 0.3 mol) and borontrifluoride etherate (194 mL, 1.53 mol) were stirred with heating (90° C.) for 1 hour and cooled to 10° C. To this cooled solution, DMF (230 mL) was added drop-wise with stirring. In another 500 mL RB flask fitted with a drying tube, DMF (390 mL) was cooled to 10° C. To this cooled DMF, p-toluenesulfonyl chloride (170.0 g, 0.9 mol) was added in small portions and the mixture was allowed to stand at room temperature for 20 minutes. This mixture containing N,N'-dimethyl (chloromethylene) ammonium chloride was then added to the above reaction mixture and the mixture was stirred at room temperature for 1 hour. The dark orange-yellow solution was then poured slowly into boiling dilute HCl (0.1 N) with vigorous stirring and allowed to stand for 30 minutes. During this process, the yellow precipitate slowly became white with the formation of formononetin. The product was filtered off and washed with water. The product was further purified by recrystallization from aqueous methanol giving a yield of 80%. The melting point was 256–257° C. The 1H-NMR of this product was identical to an authentic sample of formononetin.

EXAMPLE 6

Two step Process for the Preparation of
Formononetin

Step I: Preparation of 2,4-dihydroxy-4'methoxydeoxybenzoin by borontrifluoride etherate.

In a 500 mL RB flask fitted with a refluxing condenser and drying tube, p-methoxyphenyl acetic acid (50.0 g, 0.3 mol), resorcinol (33.2 g. 0.3 mol) and borontrifluoride etherate (194 mL, 1.53 mol) were stirred with heating (90° C.) for 1 hour. The reaction mixture was then poured into NaOAc solution (12%) and the precipitated product was filtered off, washed with water and air dried. The product was further purified by recrystallization from aqueous methanol. The yield was 95% and it melted at 147–149° C.

Preparation of 2,4-dihydroxy-4'-methoxydeoxybenzoin by $POCl_3$—$ZnCl_2$ Method.

In a 500 mL RB flask fitted with a refluxing condenser and drying tube, p-methoxyphenyl acetic acid (50.0 g, 0.3 mol), resorcinol (33.2 g, 0.3 mol) and phosphorousoxychloride (139.7 mL, 230.0 g, 1.5 mol) were stirred with heating (70° C.) for 1 hour. The reaction mixture was then poured into NaOAc solution (12%) and the precipitated product was filtered off, washed with water and air dried. The product was further purified by recrystallization from aqueous methanol. The yield was 95% and it melted at 147–149° C.

Step II, Preparation of Formononetin

In a 1 L three-necked RB flask fitted with a reflux condenser, a dropping funnel and stopper 2,4-dimethoxy-4'-methoxydeoxybenzoin (50 g, 0.193 mol) was dissolved in borontrifluoride etherate (75 mL, 84.0 g, 0.59 mol) with stirring and then cooled to 10° C. To this cooled solution, DMF (150 mL) was added drop-wise with stirring. In another 500 mL RB flask fitted with a drying tube, DMF (250 mL) was cooled to 10° C. To this cooled DMF, phosphorous pentachloride ($PCl_5$, 63.3 g, 0.3 mol) was added in small portions and the mixture was allowed to stand at 55° C. for 10 minutes. This pale pink colored mixture containing N,N'-dimethyl(chloromethylene)ammonium chloride was then added to the above reaction mixture and the mixture was stirred at room temperature for 1 hour. The dark orange-yellow solution was then poured slowly into boiling dilute HCl (0.1 N) with vigorous stirring and allowed to stand for 30 minutes. During this process, the yellow precipitate slowly became white with the formation of formononetin. The product was filtered off and washed with water. The product was further purified by recrystallization from aqueous methanol giving a yield of 85%. The melting point was 256–257° C. The $^1$H-NMR of this product was identical to an authentic sample of formononetin.

EXAMPLES 7, 8, 9 AND 10

In a similar two step process to that of Examples 6, formononetin was prepared by replacing phosphorous pentachloride (PCl$_5$) with methanesulfonylchloride (CH$_3$SOCl$_2$), phosphorous oxychloride (POCl$_3$) and p-toluenesulfonyl chloride (CH$_3$-C$_6$H$_4$-SOCl$_2$) (as described in Examples 3–5).

Thus the present invention particularly provides a process for the preparation of formononetin which involves the preparation of the starting material p-methoxy phenylacetic acid followed by its conversion to formononetin either by a "one pot" method or by a two step method involving the initial preparation of 2,4-dihydroxy-4'-methoxydeoxybenzoin. p-Methoxyphenylacetic acid is prepared by a modified method of Willgerodt reaction.

In the "one pot" method, the initial product 2,4-dihydroxy-4'-methoxydeoxybenzoin obtained by borontrifluoride method is directly converted to formononetin by treating with DMF containing N,N'-dimethyl (chloromethylene)ammonium chloride. The generation of this intermediate was accomplished by the action of either methane sulfonyl chloride, phosphorous oxychloride, phosphorous pentachloride or p-toluene sulfonyl chloride with DMF.

The two step process involves the initial preparation of 2,4-dihydroxy-4'-methoxydeoxybenzoin. The Fridel Crafts acylation of resorcinol with p-methoxyphenylacetic acid is carried out either in borontrifluoride etherate or POCl$_3$—ZnCl$_2$ mixture. Another two step process involves the conversion of 2,4-dihydroxy-4'-methoxydeoxybenzoin to formononetin by treating it with borontrifluoride etherate and DMF containing N,N'-dimethyl(chloromethylene) ammonium chloride. The generation of this intermediate was accomplished by the action of either methane sulfonyl chloride, phosphorous oxychloride, phosphorous pentachloride or p-toluenesulfonyl chloride with DMF. The purification methods make chromatographic separation unnecessary.

It is intended that the foregoing description be only illustrative of the present invention and that the present invention only be limited by the hereinafter appended claims.

We claim:

1. A process for the preparation of a isoflavone which comprises:

(a) adding a preformed N,N'-dimethyl(chloromethylene) ammonium chloride to a 2-hydroxydeoxybenzoin in a Lewis acid as a solvent to produce the isoflavone; and (b) separating the isoflavone from the reaction mixture.

2. A process for producing an isoflavone which comprises:

(a) reacting in a reaction mixture a ketone of the formula:

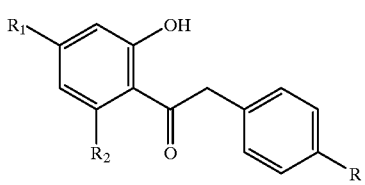

with preformed N,N'-dimethyl(chloromethylene) ammonium chloride in borontrifluoride etherate as a solvent where R is selected from the group consisting of hydrogen, hydroxyl and methoxy, R$_1$ is selected from the group consisting of hydrogen and hydroxyl and R$_2$ is selected from the group consisting of methoxy, hydrogen and hydroxyl to produce an isoflavone of the formula:

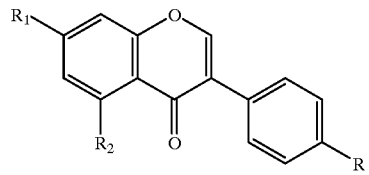

wherein R, R$_1$ and R$_2$ are as set forth previously; and (b) separating the isoflavone from the reaction mixture.

3. The process of claim 2 wherein R is methoxy, R$_1$ is hydroxy and R$_2$ is hydrogen.

4. The process of any one of claims 2 or 3 wherein the reaction is conducted at between about 10° and 100° C.

5. The process of claim 2 wherein the N,N'-dimethyl (chloromethylene) ammonium chloride is prepared by reacting dimethylformamide with a chlorinated compound selected from the group consisting of phosphorus pentachloride, phosphorus oxychloride, methanesulfonyl chloride and p-toluenesulfonyl chloride.

6. The process of claim 5 wherein the chlorinated compound is phosphorus pentachloride.

7. The process of claim 5 wherein the chlorinated compound is phosphorus oxychloride.

8. The process of claim 5 wherein the chlorinated compound is methanesulfonyl chloride.

9. The process of claim 5 wherein the chlorinated compound is p-toluenesulfonyl chloride.

10. The process of claim 5 wherein the reaction is conducted at between about 10° and 100° C.

11. A process for the preparation of formononetin which comprises:

(a) reacting resorcinol with p-methoxy phenylacetic acid in the presence of a Lewis Acid to form 2,4-dihydroxy-4-methoxydeoxybenzoin;

(b) reacting the 2,4-dihydroxy-4-methoxy benzoin with preformed N,N'-dimethylene(chloromethylene) ammonium chloride in borontrifluoride etherate to produce the formononetin; and (c) separating the formononetin.

12. The process of claim 11 wherein the Lewis acid is BF$_3$ etherate.

13. The process of claim 11 wherein the p-methoxy phenylacetic acid is prepared from a reaction of 4-methoxyacetophenone with morpholine and sulfur in a reaction mixture, then the addition of sodium hydroxide and then the addition of acid both in absence of an organic solvent.

14. The process of any one of claims 11, 12 or 13 wherein the reaction steps (a) and (b) are conducted in a single reaction vessel.

15. The process of any one of claims 11, 12 or 13 wherein steps (a) and (b) are conducted in a separate reaction vessel.

16. The process of claim 11 wherein the formononetin is separated from the reaction mixture.

17. The process of claim 11 wherein the N,N'-dimethyl (chloromethylene)ammonium chloride is prepared by reacting dimethylformamide with a chlorinated compound selected from the group consisting of phosphorus pentachloride, phosphorus oxychloride, methanesulfonyl chloride and p-toluenesulfonyl chloride.

18. The compound of claim 11 wherein the chlorinated compound is phosphorus pentachloride.

19. The compound of claim 11 wherein the chlorinated compound is phosphorus oxychloride.

20. The compound of claim 11 wherein the chlorinated compound is methanesulfonyl chloride.

21. The compound of claim 11 wherein the chlorinated compound is p-toluenesulfonyl chloride.

22. The process of any one of claims 11, 12 or 13 wherein the reaction of step (b) is conducted at between 10° and 100° C.

23. The process of claim 11 wherein the reaction of step (a) is conducted at 10° to 100° C. and the reaction of step (b) is conducted at 10° to 100° C.

* * * * *